United States Patent [19]

Ueno

[11] Patent Number: 5,132,298
[45] Date of Patent: Jul. 21, 1992

[54] DIURESIS BY CYCLODEXTRINS AND THEIR DERIVATIVES

[75] Inventor: Ryuji Ueno, Hyogo, Japan

[73] Assignee: K.K. Ueno Seiyaku Oyo, Osaka, Japan

[21] Appl. No.: 599,607

[22] Filed: Oct. 18, 1990

[30] Foreign Application Priority Data

Nov. 15, 1989 [JP] Japan ................................ 1-298091

[51] Int. Cl.$^5$ ............................................. A61K 31/715
[52] U.S. Cl. ........................................ 514/58; 514/869; 536/103
[58] Field of Search ................. 514/58, 869; 536/103

[56] References Cited

U.S. PATENT DOCUMENTS 4,258,180  3/1981  Lewis et al. ........................ 536/122
4,877,778  10/1989  Carpenter et al. .................. 536/103

FOREIGN PATENT DOCUMENTS 293537  12/1988  European Pat. Off. .
59-10525  1/1984  Japan .

OTHER PUBLICATIONS

Chemical Abstracts, vol. 98, No. 9, Feb. 28, 1983, p. 52, abstract No. 65432k, Columbus, Ohio, US; J. Serfozo et al.: "Renal effects of parenterally administered methylated cyclodextrins on rabbits".
Pharm Tech Japan, 4(2), 59(183)–65(189), (1988).
Separation and Purification Methods, 10(2), 159–237, (1981).
Tetrahedron, 24, 803–821, 1968.
Tetrahedron, 39(9), 1417–1474, 1983.

*Primary Examiner*—Ronald W. Griffin
*Attorney, Agent, or Firm*—Sughrue, Mion, Zinn, Macpeak & Seas

[57] ABSTRACT

A method for improvement in diuresis which comprises administering, to a subject in need of such improvement, a cyclodextrin or a derivative thereof in an amount effective to cause such improvement.

3 Claims, No Drawings

DIURESIS BY CYCLODEXTRINS AND THEIR DERIVATIVES

BACKGROUND OF THE INVENTION

1. Field of the Invention

The present invention relates to a method for improvement in diuresis which comprises administering a cyclodextrin or a derivative thereof to a subject.

Such improvement is required in the situation in which subjects show e.g. anuria or oliguria.

Anuria refers to a state wherein daily micturination is less than 100 ml and oliguria to a state wherein daily micturination is between 100 and 400 ml. Anuria and oliguria include those of prerenal, renal and prostrenal nature.

Prerenal anuria is caused by decrease in the renal bloodstream and originated from cardiac insufficiency, cirhosis, dehydration, shock etc. as the incentive. Renal oliguria is caused by different renal diseases. Acute nephritis and nephrotic syndrome are due to reduced glomerular filtration and enhanced tubular resorption of sodium ion and water. Acute renal insufficiency (acute tubulorrhexis) is principally caused by reduced glomerular filtration.

Since anuria and oliguria destroy the equilibrium in the body fluid and may be the causes leading to edema, uremia, cardiac insufficiency, hypertensive encephalopathy, retinitis etc., treatment of them is required.

Moreover, even in the case where the the amount of urine is normal, diuretics are often used in the treatment of cardiovascular diseases or renal diseases hypertension, edema etc.

As a result of extensive studies about the properties of cyclodextrin and their derivatives which have been used only as a complexing agent in the pharmaceutical field, the present inventor discovered that these compounds have beneficial diuretic action.

SUMMARY OF THE INVENTION

In a first aspect, the present invention provides a method for improvement in diuresis which comprises administering, to a subject in need of such improvement, a cyclodextrin or a derivative thereof (hereinafter, referred to as the compound used in the invention) in an amount effective to cause such improvement.

In a second aspect, the present invention provides a use of a cyclodextrin or a derivative thereof for the manufacture of a medicament for improvement in diuresis.

In a third aspect, the present invention provides a pharmaceutical composition for improvement in diuresis comprising a cyclodextrin or a derivative thereof in association with a pharmaceutically acceptable carrier, diluent or excipient.

DETAILED DESCRIPTION OF THE INVENTION

As used herein, the term "diuresis" refers to increased extracorporeal excretion of water, electrolytes, final metabolites etc. Usually, such excrition results in increase in the amount of urine. The compounds used in the invention have an action of increasing water secretion and secreting electrolytes. Increase in creatinine clearance (glomerular filtration) has also been confirmed indicating that the compounds used in the invention have also a action of increasing renal blood stream and glomerular filtration. The compounds used in the invention are indicated for the treatment of renal hypofuction, anuria, oliguria, hypertension of various etiologies, edema derived from various causes, promotion of drug excretion when drug intoxication is occurred, adjustment of the pressure and amount of aqueous humor or cerebrospinal fluid etc. Also, the compounds used in the invention are indicated for treatment of renal insufficiency by e.g. acute tubulorrhexis, necrosis of renal cortex etc. and nephritis.

The term "treatment" includes prevention, cure and relief of disease and arrest or relief of development of disease.

The term "cyclodextrin" includes α-cyclodextrin, β-cyclodextrin and γ-cyclodextrin.

The term "derivatives" used in conjunction with the term cyclodextrin refers to compounds in which at least one atom selected from hydrogen, oxygen or carbon in the cyclodextrin molecule is replaced by an atom or a group of atoms ordinarily present as a substituent in this kind of organic compounds (saccharides). These derivatives include etherified cyclodextrins, branched cyclodextrins, acylated cyclodextrins and sulfur-containing cyclodextrins.

Said etherified cyclodextrins include (lower)alkylcyclodextrins such as methylcyclodextrin, ethylcyclodextrin, propylcyclodextrin, dimethylcyclodextrin, trimethylcyclodextrin etc., (lower)alkenylcyclodextrins, hydroxy(lower)alkylcyclodextrins such as hydroxyethylcyclodextrin, hydroxypropylcyclodextrin etc., (lower)alkoxy(lower)alkylcyclodextrins, aralkylcyclodextrins such as benzylcyclodextrin etc., halo(lower)alkylcyclodextrins such as chloroethylcyclodextrin etc., and cylodextrinepichlorohydrine copolymer and so on. These may be etherified cyclodextrins in which one, two or three hydroxy groups in any of the glucose units of the cyclodextrin molecule are converted into ether.

Said branched cyclodextrins include glucosylcyclodextrin, maltosylcyclodextrin etc.

Said acylated cyclodextrins include (lower)alkanoylcyclodextrins such as formylcyclodextin, acetylcyclodextrin etc., aromatically or heterocyclically acylated cyclodextrins such as benzoylcyclodextrin, nicotinoylcyclodextrin etc.

Said sulfur-containing cyclodextrins include sulfonated cyclodextrins etc.

The derivatives of cyclodextrin include also derivatives in which two or more of derivatizations selected from etherification, branching, acylation and sulfuration are co-existing.

These derivatives are known or can be prepared by a method similar to that for the known derivatives.

While the dosage of cyclodextrin or derivatives thereof will vary depending on age, weight, condition of particular subject, desired therapeutic effect etc., satisfactory effects will generally be obtained with the dosage of 1 μg/kg to 500 mg/kg, preferably 10 μg/kg to 50 mg/kg, administered once a day or 2 to 4 divided doses a day or as a sustained form. Administration may be effected by injection etc.

For administration, the compound used in the invention can be given in the form of conventional pharmaceutical preparation which contains said compound, as an active ingredient, in admixture with a pharmaceutically acceptable carrier such as organic or inorganic, solid or liquid excipients suitable for the desired mode of administration such as injection. Such preparation may be in a solid form such as solid from which a solution can be made up before use, etc. or in a liquid form such as solution, emulsion, suspension, etc. Said carrier includes starch, lactose, glucose, sucrose, dextrin cellulose, paraffin, aliphatic glyceride, water, alcohol, acacia etc. The above preparation may also contain auxiliary substance, stabilizer, emulsifier, lubricant, binder, pH-adjuster, isotonic agent and other conventional additives added as necessary.

The present invention is illustrated in more detail by way of the following Examples and Test Examples.

EXAMPLE 1

| | | |
|---|---|---|
| Dimethylcyclodextrin | | 100 mg |
| Physiological saline | q.s. to | 10 ml |

The above ingredients are brought into solution by conventional way to form an injectable solution.

TEST EXAMPLE 1

Beagle dogs (weight: 7–8 kg) were alloted into groups. The animals were kept away from foods and water before 17 hours of administration of test compositions. The Ringer solution (25 mg/kg) was intravenously administered over one hour (for water-loading) and, after 30 minutes, a solution of dimethyl-α-cyclodextrin [a mixture mainly pentakis[2,6-di-O-methyl)-mono(2,3,6-tri-O-methyl)-α-cyclodextrin; hereinafter referred to as DMCD] (5 mg/kg) in the Ringer solution was intravenously administered. The control group received the same amount of Ringer solution.

Urine samples were collected using catheter at 30 minutes intervals and assayed for the amount of electrolytes (sodium, potassium and chloride). Also, the total amounts of excretion of each items, respectively, from the time of administration and up to 120 minutes thereafter were measured. The results are shown in Table 1. In addition, urine and serum creatinine concentrations were measured at appropriate time from which values of creatinine clearance (glomerular filtration) were calculated. The results are shown in Table 2.

TABLE 1

| | Urine(ml) | Na(mEq) | K(mEq) | Cl(mEq) |
|---|---|---|---|---|
| Control (n = 6) | 26.9 ± 19.3 (S.D.) | 4.4 ± 2.2 | 1.3 ± 0.5 | 4.9 ± 1.7 |
| DMCD (n = 3) | **61.3 ± 3.6 | *12.7 ± 3.0 | *3.8 ± 1.1 | *13.6 ± 3.1 |

Dannet Method:
*P < 0.01,
**P < 0.05

TABLE 2

| | Creatinine Clearance (ml/kg/min) | |
|---|---|---|
| | After: | |
| | 60 min | 120 min |
| Control (n = 6) | 2.47 ± 0.76 (S.D.) | 2.67 ± 0.74 |
| DMCD (n = 3) | **3.83 ± 0.63 | 3.50 ± 0.29 |

TEST EXAMPLE 2

Male rats (Crj; weight 100–150 g) were alloted into groups. After receiving test compositions, they were bred in cages. Cumulative amount of urine was weighed after 3 hours without food and water (3 hr Urine) and after additional 21 hours with food and water (21 hr Urine), giving 24 hr urine as the total amount. Further, 21 hr urine was assayed for osmotic pressure using an osmometer (OM-801, Asahi Lifescience). As the test compounds were used DMCD, hexakis(2,6-O-methyl-α-cyclodextrin [purified from DMCD as a mixture; hereinafter referred to as Compound I] and pentakis(2,6-di-O-methyl)-mono(2,3,6-tri-O-methyl)-α-cyclodextrin [purified from DMCD as a mixture; hereinafter referred to as Compound II], dissolved in the physiological saline and administered at a rate of 5 mg/kg via a caudal vein. The control group received the physiological saline. The results are shown in Table 3.

TABLE 3

| | Urine(ml) | Osmotic Pressure(osm/kg) |
|---|---|---|
| Control (n = 6) | 10.5 ± 1.3 (S.D.) | 2.23 ± 0.55 |
| DMCD 1 mg/kg (n = 3) | 16.0 ± 2.2 | 1.40 ± 0.17 |
| Compound I 1 mg/kg (n = 3) | 14.0 ± 4.0 | 1.65 ± 0.41 |
| Compound I 5 mg/kg (n = 3) | 15.4 ± 1.4 | 1.41 ± 0.23 |
| Compound II 2 mg/kg (n = 3) | 14.0 ± 5.2 | 1.68 ± 0.65 |
| Compound II 5 mg/kg (n = 3) | 16.4 ± 0.8 | 1.31 ± 0.39 |

The above results indicate that the compounds used in the invention have excellent diuretic action.

What is claimed is:
1. A method for improvement in diuresis which comprises administering, to a subject in need of such improvement, an etherified cyclodextrin as a biologically active material to cause diuresis in an amount effective to cause such improvement.
2. A method according to claim 1, in which the etherified cyclodextrin is selected from the group consisting of dimethylcyclodextrin.
3. A method according to claim 1, in which the etherified cyclodextrin is selected from the group consisting of etherified α-cyclodextrin.

* * * * *